United States Patent [19]

Binnig et al.

[11] Patent Number: 4,459,301
[45] Date of Patent: Jul. 10, 1984

[54] METHOD OF TREATING CARDIAC DISORDERS USING BISPIDINE DERIVATIVES

[75] Inventors: Fritz Binnig, Fussgoenheim; Claus D. Mueller, Viernheim; Manfred Raschack, Weisenheim am Sand; Gerda von Philipsborn, Weinheim, all of Fed. Rep. of Germany

[73] Assignee: BASF Aktiengesellschaft, Fed. Rep. of Germany

[21] Appl. No.: 354,515

[22] Filed: Mar. 3, 1982

[30] Foreign Application Priority Data

Mar. 27, 1981 [DE] Fed. Rep. of Germany ....... 3112055

[51] Int. Cl.³ ............................................. A61K 31/445
[52] U.S. Cl. ..................................... 424/267; 546/122
[58] Field of Search ........................ 546/122; 424/267

[56] References Cited

FOREIGN PATENT DOCUMENTS 2428792 1/1976 Fed. Rep. of Germany .
2658558 6/1978 Fed. Rep. of Germany .
2726571 12/1978 Fed. Rep. of Germany .

OTHER PUBLICATIONS

Horlein, Eur. J. Med. Chem. (1977), pp. 301-303.
J. Med. Chem. 20, (1977), pp. 1668-1671.
Journal of Medicinal Chem. 22, (1979), pp. 1142-1144.

Primary Examiner—Robert W. Ramsuer
Attorney, Agent, or Firm—Keil & Witherspoon

[57] ABSTRACT

Bispidine derivatives of the formula I

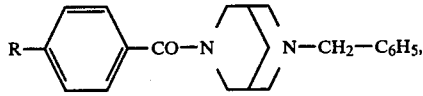

where R is hydrogen or amino, and their salts with physiologically tolerated acids. The compounds possess antiarrhythmic properties.

1 Claim, No Drawings

METHOD OF TREATING CARDIAC DISORDERS USING BISPIDINE DERIVATIVES

The present invention relates to novel bispidine derivatives, their preparation and drugs containing these novel substances.

It has been disclosed that a number of bispidine derivatives possess antiarrhythmic properties (cf. German Laid-Open Applications DOS No. 2,428,792 and DOS No. 2,726,571, and J. Med. Chem. 20 (1977), 1668).

We have found two novel bispidine derivatives which have a superior action to the known derivatives.

The present invention relates to novel bispidine derivatives of the formula I

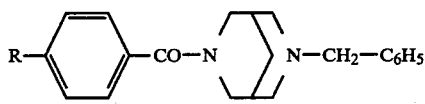

where R is hydrogen or amino, and their salts with physiologically tolerated acids.

Examples of suitable physiologically tolerated acids are hydrochloric acid, sulfuric acid, phosphoric acid, acetic acid, malonic acid, succinic acid, fumaric acid, maleic acid, citric acid, tartaric acid, lactic acid and diamidosulfonic acid.

The present invention further relates to a process for the preparation of the bispidine derivatives of the formula I and their salts with physiologically tolerated acids, wherein N-monobenzylbispidine is reacted with a compound of the formula II

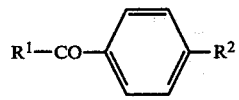

where $R^1$ is halogen and $R^2$ is hydrogen or nitro, and, if $R^2$ is nitro, the latter is reduced, and the compound thus obtained is converted, if desired, into its salt with a physiologically tolerated acid.

The reaction of N-monobenzylbispidine with the compound II can be carried out, for example, with sodium hydride in dimethylformamide, sodium hydroxide in water or ethanol, sodium carbonate in butanol or amyl alcohol, potassium carbonate in water, methanol, ethanol, isopropanol, butanol, amyl alcohol, acetone, acetonitrile, toluene, dimethylformamide, dimethylsulfoxide or tetrahydrofuran, sodium methylate in methanol, sodium isopropylate in isopropanol, potassium tert.-butylate in tert.-butanol, tetrahydrofuran or dimethylsulfoxide, or sodium amide in toluene or xylene, most advantageously with sodium hydride in dimethylformamide. As a rule the reaction is carried out at room temperature.

If a nitro group is present, it is most advantageous to reduce it catalytically with hydrogen, using in particular a platinum catalyst.

Suitable solvents are lower alcohols, in particular ethanol.

Finally, the present invention relates to drugs which contain the bispidine derivatives of the formula I or their salts with physiologically tolerated acids.

The novel compounds may be administered orally or parenterally (intravenously, intramuscularly or intraperitoneally), in a conventional manner.

The dosage depends on the age, condition and weight of the patient and on the administration route. As a rule, the daily dose of active compound is from about 0.5 to 10 mg/kg of body weight for oral administration and from about 0.01 to 1.0 mg/kg of body weight for parenteral administration. Normally, satisfactory results are achieved with daily doses of from 1 to 5 mg/kg administered orally and from 0.02 to 0.1 mg/kg administered parenterally.

The novel compounds may be employed in the conventional solid or liquid pharmaceutical forms, for example as tablets, film tablets, capsules, powders, granules, coated tablets, suppositories or solutions. They are prepared in a conventional manner, by compounding the active compounds with the conventional pharmaceutical auxiliaries, such as tablet binders, fillers, preservatives, tablet disintegrating agents, flow regulators, plasticizers, wetting agents, dispersants, emulsifiers, solvents, retarders and/or antioxidants (cf. L. G. Goodman and A. Gilman: The Pharmacological Basis of Therapeutics). The pharmaceutical products thus obtained normally contain from 0.1 to 99% by weight of the active compound.

The novel compounds and their physiologically tolerated addition salts with acids have a powerful antiarrhythmic action and are therefore particularly useful for the pharmacotherapy of arrhythmias.

The antiarrhythmic activity of the compound according to the invention is determined on isolated left atria of male guinea pigs (Pirbright white, weight 350 to 450 g). Atria suspended in an organ bath (volume 125 ml) containing carbogen (95% $O_2$/5% $CO_2$)-saturated Tyrode's soluton (pH 7.4, 32° C.) are prestressed with 1.0 g and are driven by square wave pulses of 1 Hz base rhythm and double stimulation threshold values (rheo base: 0.2 to 1.4 V, chronaxia: 0.3 to 0.5 msec). As a criterion of the antiarrhythmic activity, the frequency (in Hz) at which the atria are just still able to follow the sequence of pulses (the maximum driving rate) is determined by automatic continuous increase in frequency. The concentration which produces a 50% decrease in maximum driving rate, ie. the EC 50% is calculated from the linear relationship between log concentration (mg/l) of the active substance and relative decrease in maximum driving rate ($\Delta\%$).

Furthermore, the concentration which produces a 25% decrease in contraction amplitude, ie. the EC 25%, is determined, as a measure of the negatively inotropic effect, from the linear relationship between log concentration (mg/l) and relative change in contraction amplitude ($\Delta\%$).

Moreover, the antiarrhythmic activity of the novel substances is determined on male rats (Sprague Dawley, weight 200 to 230 g), after oral administration. 45 minutes after administration of the substance, the animals are anesthetized with sodium thiobutabarbital (100 mg/kg, administered intraperitoneally). Aconitine is used as the arrhythmogenic substance, and is infused intravenously at a rate of 0.005 mg/kg per min, 60 minutes after administration of the test substance. In untreated animals (N=52), the ECG shows arrhythmias after 2.74±0.07 minutes, and the onset of these can be delayed by antiarrhythmics in dependence on the dose. The dose which prolongs the infusion time by 50%, ie. the ED 50%, is determined from the linear relationship between log dose (mg/kg) of the test substance and the relative prolongation of the aconitine infusion time (%).

Further, the dose at which toxic symptoms (changes in the initial ECG, cyanosis or cramp) occur is determined. The quotient of the acute toxic dose and the antiarrhythmic ED 50% is therefore determined as a measure of the toleration.

The novel compounds are further characterized by investigating whether, in addition to antiarrhythmic properties, stimulating effects on smooth muscle, which may lead to undesirable side effects (hypertension or stimulation of the uterus), are detectable. The concentration (mol/l) which achieves 50% of the contraction obtained with a previously tested noradrenalin concentration ($10^{-6}$ mol/l), ie. the EC 50%, is determined on spiral strips of rat aorta suspended in an organ bath containing carbogen-saturated Krebs Henseleit solution at 37° C.

Moreover, the effect of the compound according to the invention on the systolic and diastolic blood pressure of unanesthetized dogs on intravenous administration is tested.

The known antiarrhythmic compounds N,N'-bisbenzylbispidine (B, German Laid-Open Application DOS No. 2,428,792), N-benzyl-N'-(2,2-diphenylethyl)-bispidine (A, German Laid-Open Application DOS No. 2,726,571) and sparteine were used as comparative substances.

N-(4-Aminobenzoyl)-N'-benzylbispidine (C) has a powerful antiarrhythmic effect on isolated guinea pig atria (Table 1) and causes a decrease in the maximum driving rate, similarly to the reference substances. It should be particularly noted that these substances cause a relatively small decrease in the force of contraction. The interval between the desired antiarrhythmic effect and the undesired negatively inotropic effect, which is evident from the quotient EC 25% (decrease in force of contraction)/EC 50% (decrease in maximum driving rate), is thus 4 or 5 times greater for the novel compound than for the comparative compounds.

The antiarrhythmic activity of the novel compound on the aconitine-induced arrhythmia in rats (Table 2) is about 4 times that of reference substance B, twice that of reference substance A, and 18 times that of sparteine, with about twice the difference or about the same difference, respectively, between toxic and antiarrhythmic doses.

A further advantage of the novel compound is the lack of stimulating effects on smooth muscle (Table 3). In contrast to reference substance B and sparteine, Example 1, even in very high concentrations ($3 \cdot 10^{-4}$ mol/l), has no constrictive effect on the vascular muscle in vitro. This difference obviously also applies to the intact organism. In contrast to reference substance B and sparteine (Table 4), which cause a substantial increase in the systolic and in particular in the diastolic blood pressure, the novel compound has no hypertensive effect. This leads to a better toleration in the therapy of arrhythmias.

TABLE 1

| | Effect on isolated guinea pig atrium | | | | |
|---|---|---|---|---|---|
| | Maximum driving rate | | Force of contraction | | |
| Substance | EC 50%[a] | R.A.[b] | EC 25%[c] | R.A. | Q[d] |
| C | 6.14 | 0.96 | 100 | 0.22 | 16.3 |
| A | 1.43 | 3.93 | 4.92 | 4.43 | 3.44 |
| B | 5.92 | 1.00 | 21.8 | 1.00 | 3.68 |

[a] Concentration (mg/l) which causes a 50% decrease in the maximum driving rate
[b] R.A. = relative activity: reference substance B = 1.00
[c] Concentration (mg/l) which causes a 25% decrease in the force of contraction
[d] $Q = \frac{EC\ 25\%}{EC\ 50\%}$

TABLE 2

| | Antiarrhythmic effect and toxicity in the rat (oral admin.) | | | |
|---|---|---|---|---|
| | Effective dose | | | |
| Substance | EC 50%[a] | R.A.[b] | Toxic dose | Q[d] |
| C | 6.37 | 3.56 | 46.4 | 7.3 |
| A | 13.0 | 1.75 | 100 | 7.7 |
| B | 22.7 | = 1.00 | 100 | 4.4 |
| Sparteine | 112 | 4.93 | 464 | 4.1 |

[a] dose (mg/kg) which prolongs the aconitine infusion time by 50%
[b] R.A. = relative activity: reference substance B = 1.00
[c] Dose (mg/kg) after whose administration the first toxic symptoms are observed
[d] $Q = \frac{toxic\ dose}{ED\ 50\%}$

TABLE 3

| Constrictive effect on isolated strips of rat aorta | |
|---|---|
| Substance | EC 50 mol/l |
| C | —[a] |
| Sparteine | $5.51 \cdot 10^{-4}$ |
| B | $3.8 \cdot 10^{-6}$ |

[a] No effect up to $3 \cdot 10^{-4}$ mol/l

TABLE 4

| Effect on the blood pressure of unanesthetized dogs (intravenous administration) | | | |
|---|---|---|---|
| | | Change in blood pressure ($\Delta$ mm Hg) | |
| Substance | mg/kg | systolic | diastolic |
| C | 2.0 | −5 | −2 |
| B | 2.0 | +20 | +59 |
| Sparteine | 5.0 | +19 | +40 |

The Examples which follow illustrate the invention.

EXAMPLE 1

(a) N-(4-Nitrobenzoyl)-N'-benzylbispidine 18.8 g (0.43 mol) of a 55% strength sodium hydride suspension are added to a solution of 84.7 g (0.392 mol) of monobenzylbispidine in 800 ml of dimethylformamide. The mixture is stirred for 5 hours at room temperature, after which a solution of 72.7 g (0.392 mol) of 4-nitrobenzoyl chloride in 200 ml of dimethylformamide is added dropwise, and stirring is continued for 3 hours. The excess sodium hydride is decomposed using methanol, the solvent is distilled off under reduced pressure, the residue is taken up in water, and the solution is extracted immediately with ether. The organic phase is dried with sodium sulfate, the ether is evaporated, and a residue of 118.0 g (82.5%) of N-(4-nitrobenzoyl)-N'-benzylbispidine of melting point 125° to 127° C. is obtained.

(b) N-(4-Aminobenzoyl)-N'-benzylbispidine 1,5-fumarate 118.0 g of N-(4-nitrobenzoyl)-N'-benzylbispidine are dissolved in 1,700 ml of ethanol, 5 g of 5% strength Pt/C are added, and hydrogenation is carried out in a 2 l flask, with stirring. After completion of the absorption of hydrogen, the mixture is filtered off from the catalyst and evaporated down. The residue is dissolved in 1,000 ml of hot isopropanol, and 56.2 g of fumaric acid are added. On cooling the solution, 124.0 g (81%) of N-(4-aminobenzoyl)-N'-benzylbispidine 1,5-fumarate of melting point 151°–153° C. crystallize out.

EXAMPLE 2

By a similar procedure to that of Example 1(a), N-benzoyl-N'-benzylbispidine sulfate of melting point 181° C. is obtained in a yield of 76.2%.

EXAMPLE 3

Tablets of the following composition are obtained in a conventional manner, using a tablet press:
50 mg of N-(4-aminobenzoyl)-N'-benzylbispidine,
120 mg of corn starch,
13.50 mg of gelatine,
45 mg of lactose,
22.5 mg of talc,
2.25 mg of Aerosil ® (chemically pure, finely divided silica containing submicroscopic particles), and
6.75 mg of potato starch (as a 6% strength paste)

EXAMPLE 4

Coated tablets of the following composition are prepared in a conventional manner:
30 mg of N-benzoyl-N'-benzylbispidine,
60 mg of core material, and
60 mg of sugar-coating mixture.

The core material consists of 9 parts of corn starch, 3 parts of lactose and 1 part of Luviskol ®VA 64 (60:40 vinylpyrrolidone/vinyl acetate copolymer, cf. Pharm. Ind. 1962, 586). The sugar-coating mixture consists of 5 parts of sucrose, 2 parts of corn starch, 2 parts of calcium carbonate and 1 part of talc. The coated tablets thus prepared are then provided with a final coating which is resistant to gastric juices.

EXAMPLE 5

10 g of N-(4-aminobenzoyl)-N'-benzylbispidine are dissolved in 5,000 ml of water, with the addition of NaCl and an equimolar amount of acetic acid, so that a blood-isotonic solution results. 5 ml of the solution are introduced into each ampoule and the ampoules are sterilized.

We claim:

1. A method of treating cardiac disorders which comprises administering orally or parenterally to the patient an effective amount of a composition comprising a pharmaceutically acceptable solid or liquid carrier and from 0.1 to 99 percent by weight of a compound of the formula I

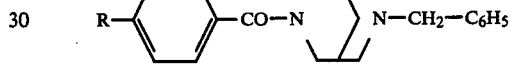

where R is amino, and its salts with physiologically tolerated acids.

* * * * *